United States Patent [19]
Riess

[11] Patent Number: 5,597,309
[45] Date of Patent: Jan. 28, 1997

[54] METHOD AND APPARATUS FOR TREATMENT OF GAIT PROBLEMS ASSOCIATED WITH PARKINSON'S DISEASE

[76] Inventor: Thomas Riess, 176 Morningside Ct., San Anselmo, Calif. 94960

[21] Appl. No.: 218,669

[22] Filed: Mar. 28, 1994

[51] Int. Cl.6 .................................................. G09B 19/00
[52] U.S. Cl. ......................... 434/258; 434/307 R; 434/365
[58] Field of Search .............................. 434/44, 112, 118, 434/236, 238, 247, 250, 252, 255, 258, 307 R, 365; 79/379.01, 379.04; 364/413.01, 413.02; 345/7, 8, 123; 273/77 R, 87.2, 440, 448, 654; 601/23, 27–29; 128/731, 732, 740, 774, 782; 482/8, 900–902; 351/210, 203

[56] References Cited

U.S. PATENT DOCUMENTS

| | | | |
|---|---|---|---|
| 2,605,557 | 8/1952 | Van Deventer | 434/250 |
| 4,631,676 | 12/1986 | Pugh | 364/413.01 |
| 4,688,037 | 8/1987 | Krieg | 434/112 X |
| 4,714,919 | 12/1987 | Foster | 345/123 |
| 4,762,131 | 8/1988 | Okuda | 434/258 X |
| 4,906,193 | 3/1990 | McMullen et al. | 434/258 |
| 5,003,300 | 3/1991 | Wells | 345/8 |
| 5,100,328 | 3/1992 | Badgley | 434/112 X |
| 5,249,967 | 10/1993 | O'Leary et al. | 434/247 |
| 5,362,238 | 11/1994 | Slavin | 434/258 X |
| 5,374,193 | 12/1994 | Trachtman | 434/258 |

OTHER PUBLICATIONS

Marsden et al, "Success and Problems in Long–Term Levodopa Therapy in Parkinson's Disease", The Lancet, Feb. 12, 1977, pp. 345–349.
"Neurophysiology" by David Marsden, The John Hopkins University Press, 1990, pp. 57–98.
Brotchie et al, "Motor Function of the Monkey globus Pallidus", Brain, 114: 1685–1701, 1991.
Georgiu et al, "An Evaluation of the Role of Internal Cues in the Pathogenesis of Parkinsonian Hypokinesia", Brain, 116, 1575–1586,1993.
Glickstein et al, "Paradoxical Movement in Parkinson's Disease", TINS, 166 14,480–482, 1991.
Hoover et al, "Multiple Output Channels in the Basal Ganglia", Science 259, 1993.
Klockgether et al, "Visual Control of Arm Movement in Parkinson's Disease", Movement Disorders, vol.9., No. 1, 1994, pp. 48–56.
Krasilovsky et al, "Effect of Video Feedback on the Performance of a Weight Shifting controlled Tracking Task in Subjects with Parkinsonsim and Neurologically Intact Individuals", Experimental Neurology 113, 192–200, 1991.
Luquin et al, "Levodopa–Induced Dyskinesias in Parkinson's Disease: Clinical and Pharmacological Classification", Mov.Disord, vol. 7, No.2,1992,pp. 117–124.
Malapani et al, "Impaired Simultaneous Cognitive Task Performance in Parkinson's Disease: A A Dopamine–Related Dysfunction", Neurology 44:319–326, Feb. 1994.
James Purdon Martin, "The Basal Ganglia and Posture", B Lippincott Company, 1967, pp. 23–33 and 35.
"Virtual Environment Display System" by Fisher et al. ACM 1986 Workshop on Interactive 3D Graphics, Oct. 1986.

*Primary Examiner*—Joe Cheng
*Attorney, Agent, or Firm*—Dergosits & Noah

[57] ABSTRACT

A method for the treatment of gait problems associated with Parkinson's Disease in a subject involves the use of virtual cues which are delivered to the subject in a spatial orientation and at rate which enable the initiation and sustainment of ambulation, as well as the suppression of dyskinesia associated with medication. In one embodiment, a mulfiplexed head up display is used to provide the cues to the subject's field of vision without obscuring the real world. In another embodiment, light emitting diodes fastened to eye glasses are used to deliver the virtual cues to the subject's field of view.

8 Claims, 5 Drawing Sheets

SUSTAINING CUES

SUSTAINING CUES
WITH
FIXED INITIATING CUE

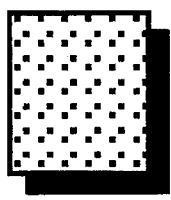
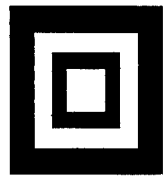
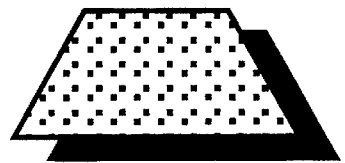
FIG. 1A     FIG. 1B     FIG. 1C
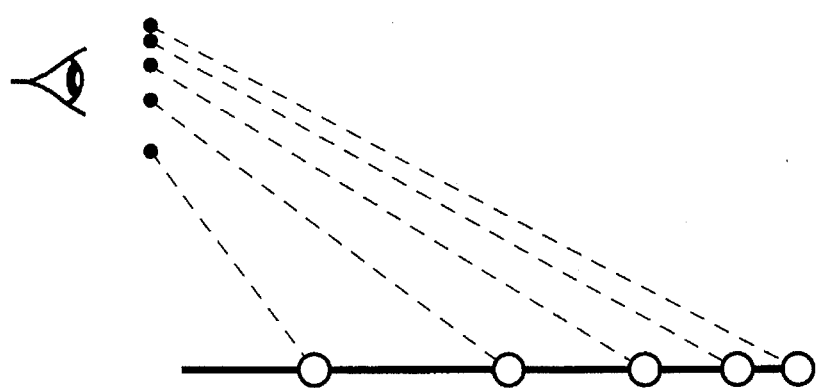
FIG. 2

PROPOSED OPTIMAL CONFIGURATION

FIG. 6A
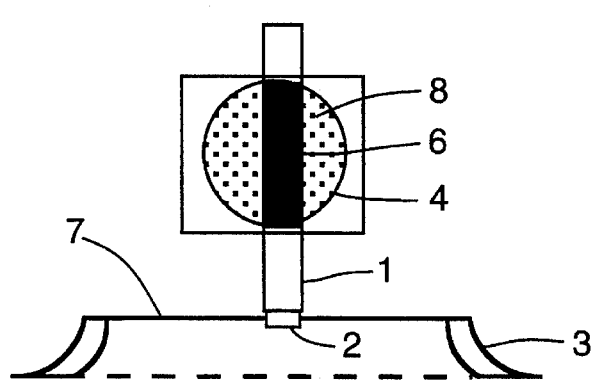
FIG. 6B
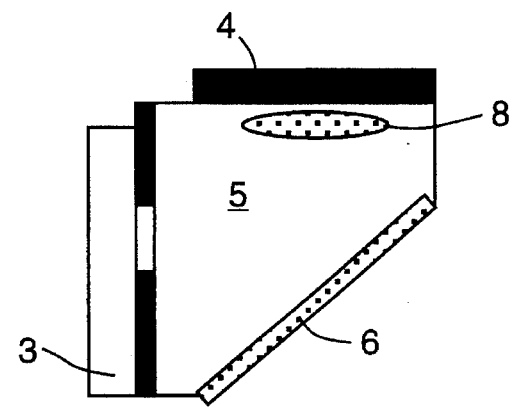
EDGE OF COL. LENS CONVEX SURFACE
TO WIDEN THE IMAGE
FIG. 6C
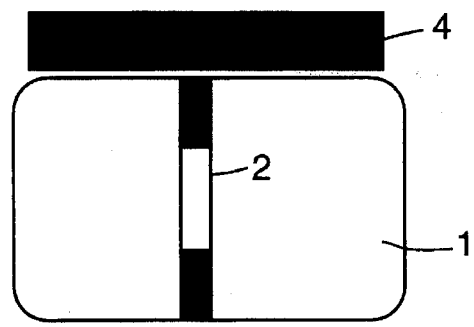
FIG. 6D

METHOD AND APPARATUS FOR TREATMENT OF GAIT PROBLEMS ASSOCIATED WITH PARKINSON'S DISEASE

TECHNICAL FIELD

The present invention relates generally to methods and apparatus for use in the treatment of gait problems experienced by subjects with Parkinson's Disease. More specifically, the present invention is directed to methods and apparatus which provide visual cues to the subject's field of view. These cues enables a subject to initiate ambulation and to sustain ambulation and also enable a subject to overcome problems associated with the chronic use of anti-Parkinson's Disease medications.

BACKGROUND OF THE INVENTION

Two of the most debilitating aspects of Parkinson's Disease are akinesia, resulting from low levels of dopamine in the brain, and dyskinesia, a consequence of long term use of drugs used in the treatment of Parkinson's Disease. The effects of low levels of dopamine on a person's mobility range from the complete inability to initiate ambulation to small little "stutter" steps (festination) to normal walk which suddenly freezes. These problems correspond to the so-called "off" periods which many Parkinson Disease subjects experience several times during the day and which result when the level of dopamine in the brain falls below therapeutic levels. Dyskinesia is a consequence of long term use of dopamine resulting in uncontrollable excessive motor activity, a kind of super sensitivity to dopamine. Dyskinesia occurs during so-called on periods in the presence of therapeutic or elevated levels of dopamine in the brain. Most people who suffer from long term Parkinson's Disease cycle between "on" and "off" periods and the related gait and motor problems several times a day.

At the preset time, attempts to control these debilitating aspects of Parkinson's Disease have centered around pharmacological and surgical approaches. Pharmacological attempts involve adjusting dosages, combinations, absorption and routes of administration of various drugs. Success is generally modest at best and transient as the disease relentlessly progresses. Surgical attempts have been made, specifically modified Ventral Pallidotomy and dopaminergic cell implantation procedures. While both pharmacological and surgical approaches offer promise neither provide a reliable solution to the debilitating aspects of the disease.

*Kinesia paradoxa* is a phenomenon which has long been reported in the literature. In the presence of so-called "visual cues" certain Parkinsonian subjects can overcome akinesia and related gait problems even when unmedicated or undermedicated. There are a variety of visual cues which are effective in evoking this response in receptive individuals. Most of these visual cues involve objects that the individual perceives as stepping over. An example of such a visual cue would be an array of ordinary playing cards on the floor at one's feet, spaced at intervals equal to or slightly greater than the subject's walking stride length and placed so as to align to his/her vector of gait.

Therefore, one of the objectives of the present invention is to provide "virtual" cues which evoke the same response as the real visual cue.

SUMMARY OF THE INVENTION

According to the present invention, virtual visual cues are provided to the patient on an "as-needed" basis, allowing them to be employed when and where necessary. The virtual cues are superimposed onto reality, i.e., the patient's ordinary field of vision. The frequency and type of cue, as well as the intercue distance can be modulated to facilitate different rates of ambulation and to function optimally in overcoming the varying types of abnormal gait associated with Parkinson's Disease as well as dyskinesia. These cues can be generated by a variety of different devices, but the cues as perceived must satisfy certain criteria in order to evoke the desired response.

The cues must be visible against the backdrop of the real world, but it must not obscure the subject's perception of their physical environment. The virtual cue is generally a two dimensional geometric shape, e.g., a square or circle in a bright color of high luminescence or contrast. The spatial orientation of the virtual cues must be perceived as being on the transverse weight-bearing surface along the vector of ambulation.

BRIEF DESCRIPTION OF THE FIGURES

FIG. 1 is a depiction of effective virtual vision cues.

FIG. 2 is a diagram of the subject's perception and the desired spatial orientation of the virtual cues.

FIG. 6 is a schematic diagram of one embodiment of the present invention in which a video image device is used to provide visual cues.

DETAILED DESCRIPTION OF THE INVENTION

Figure 3:
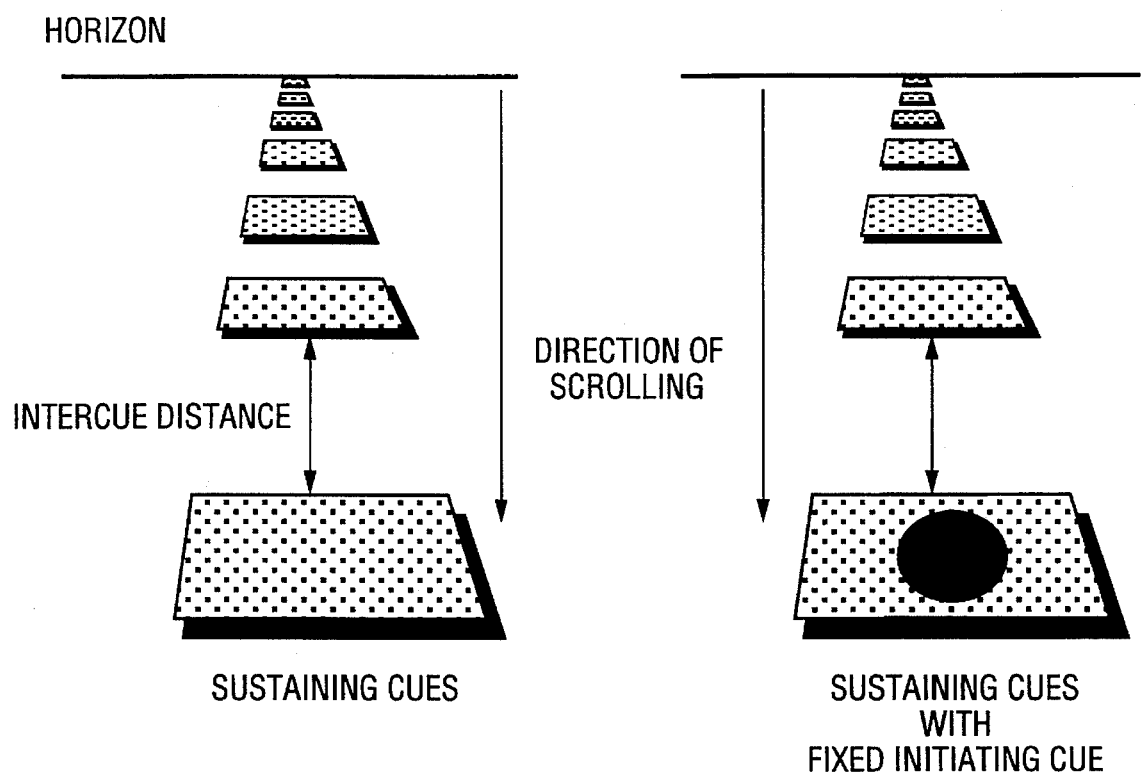
FIG. 3 is a representation of the scrolling of virtual cues used to sustain gait.

An understanding of the varying categories of gait abnormalities associated with Parkinson's Disease is necessary to appreciate the scope and optimal application of the present invention. Parkinson's Disease gait problems can be organized into two major categories. The first category includes problems associated with the pathology of Parkinson's Disease: (1) akinesia — difficulty initiating ambulation; and, (2) problems associated with sustaining ambulation — sudden freezing, (3) stutter or shuffling steps also known as festination and (4) slowness (bradykinesia). The second category involves problems associated with the long term use of anti-Parkinson's Disease drugs — dyskinesia.

Akinesia has three clinically identifiable stages. Stage 1 involves the inability to overcome the force of gravity on weight-bearing parts, e.g., the subject feels like her feet are "glued to the floor". (4) In Stage 2, the subject has difficulty in initiating a normal stride-length step. Stage 3 is typified by so-called heel walking. Stages 2 and 3 are a likely consequence of disturbance in equilibrium and perspective of one's center of gravity.

FIG. 1 shows three types of virtual cues, each of them characterized by geometric shapes with high contrast and bright colors. Background shadows and perspective can be used to give the image a three-dimensional feeling. The second cue in FIG. 1 depicts an image with varying luminance which can be useful in environments with varying lighting conditions.

FIG. 2 shows the preferred spatial orientation of virtual cues, perceived as being on the transverse weight-bearing surface.

According to the present invention, there are two types of cues used in overcoming the gait problems associated with the pathology of Parkinson's Disease (Category 1 from above.) The first type of cue is an initiating cue which serves to initiate ambulation, particularly in the more severe Stage 1 akinesia. The second type of cue is a sustaining cue which is often needed to sustain ambulation once initiated. An initiating cue is static. It appears as a single object and is perceived as passing under foot as the subject takes a first step. Sustaining ambulation requires multiple cues, at least two, and in a preferred embodiment, the cues must be sufficient in number to be perceived as extending out towards the horizon. The optimal positioning of the different types of cues is a function of the type of gait abnormality. Table 1 summarizes the relationship of various parameters.

TABLE 1

| ability to initiate | ability to sustain | type of gait sustained | initiating cue | distance of initiating cue from toes | sustaining cue | distance of first sustaining cue from toes |
|---|---|---|---|---|---|---|
| no | yes | normal | yes | ½ s.l. | no | |
| no | yes | festinating | yes | ½ s.l. | yes | 1.5 s.l. |
| no | yes | normal then freezing | yes | ½ s.l. | yes | ½ s.l. |
| no | no | | yes | directly at toes | yes | 1 ½ s.l. |
| yes | yes | festinating | no | | yes | ½ s.l. |
| yes | no | | no | | yes | ½ s.l. | s.l. = stride length

After a short learning period, most subjects can accommodate some deviation from the optimal cue locations.

Sustaining cues are kinetic and scroll toward the subject at a rate which is synchronized to his/her rate of ambulation. The intercue distance between the first and second sustaining cue is defined as that distance which allows the subject to perceive that as his foot strikes the floor at the end of a normal stride it lands midpoint between the first and second sustaining cue. The intercue distance between subsequent sustaining cues are consistent with perspective as though one would perceive real objects extending out to the horizon. See FIG. 3.

Figure 4:
FIG. 4 shows a sequence of scrolling cues useful in suppressing dyskinesia.

Sustaining cues are also effective in suppressing dyskinesia. However, an even more effective cueing pattern for suppressing dyskinesia would be a series of scrolling cues moving at approximately twice the speed of gait. See FIG. 4. Virtual cues which are used for this purpose need not be oriented in space, allowing them to appear as if they are floating at eye level.

Figure 5:
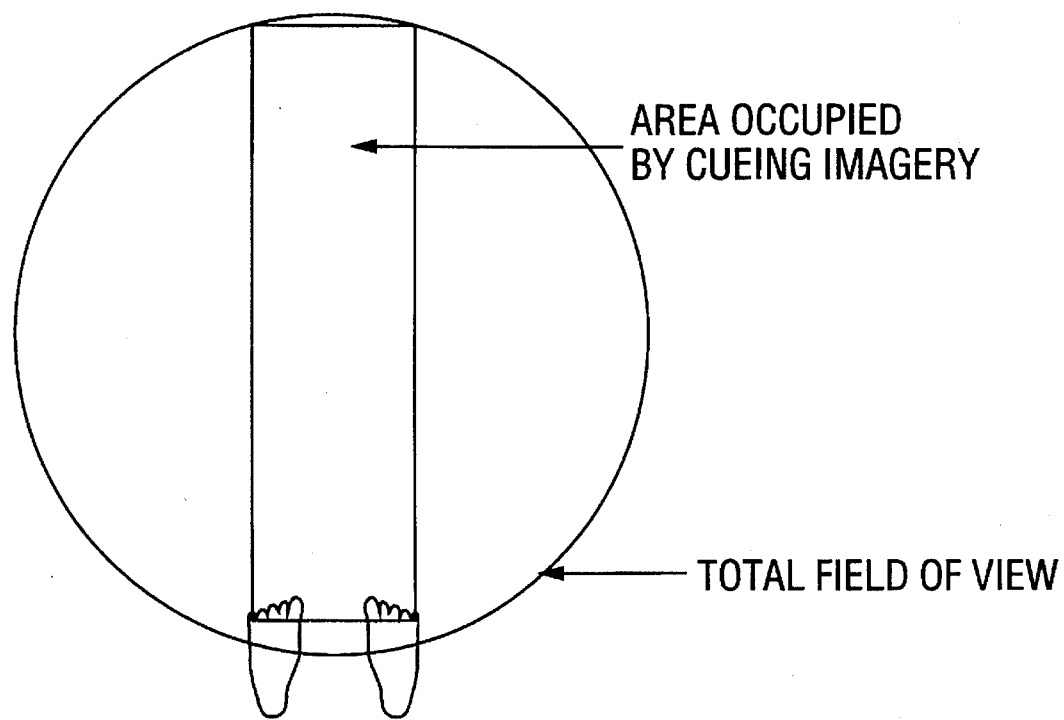
FIG. 5 is a diagram which shows the optimal field of view for viewing the virtual cues.

For each of the cues, the optimal field of view for viewing the imagery is midline in the field of view to slightly offset to the midbody side. As shown in FIG. 5, the field should optimally be rectangular and extend from bottom to the top of the field of view (from 6 to 12 o'clock).

Virtual cues are very effective in suppressing dyskinesia. The criteria for the development of virtual cues for suppressing dyskinesia are less constrained. The cues useful for this application appear not to require positioning on the transverse weight-bearing plane. Synchronized scrolling speed and intercue distance does not appear critical, with faster speeds demonstrating greater effect.

According to the present invention, the virtual cues are provided to the subject through some type of image-generating device. The device must meet certain criteria in order to be effective for this application. The device must effectively evoke the desired response. It must keep the cues visible in varied lighting conditions, including darkness and bright sun. The device must be able to modulate intercue distances and to vary scrolling speed. The device must be able to project the virtual cues onto the transverse weight-bearing surface with no or minimal extraneous visual information. The overall device must be portable and lightweight. It must be able to provide virtual cue images on demand. Any controls have to be easily adjustable to accommodate Parkinson's Disease subjects with tremor. The device must also be available at a reasonable cost. The image-generating device provides a maximum field of view along a vertical midline strip. The device must also be designed for style, i.e., it must be acceptable for the subject to wear socially.

Some of the hardware devices which are capable of meeting some of the above-listed criteria are: (1) cue cards physically attached onto the subject's footgear; (2) viewing cues through the viewfinder of a handheld video camera; (3) use of a mechanical device to scroll targets while a collimating lens works to project the focused image toward the subject's field of view; (4) strobe lights to generate transient blind spots which act as cues; (5) objects affixed to ordinary eyeglasses; (6) laser light pen; (7) a commercial field-multiplexed head-up display such as the VIRTUAL VISION™ sport eyewear(see FIG. 7); (8) an array of light emitting diodes affixed to glasses; (9) liquid crystal displays affixed to glasses; and (10) a hologram generating device with the ability to produce images at the necessary intercue distances and at the necessary rate.

One of the presently preferred embodiments consists of light emitting diodes affixed to eyeglasses.

Another embodiment involves the use of a video-based image source as shown in FIG. 6. The objectives of this embodiment are to provide (i) a means to stabilize the apparatus to the eye; (ii) a way to shield the cue image from ambient environmental light; (iii) a collimating lens which is narrow; (iv) a means for projecting the image and thereby enlarging it; and, (v) the ability to provide a wider cue image to the visual field. These objective are addressed in the device shown in FIG. 6.

The device is shown in top view in FIG. 6a. A safety glass lens 7 is surrounded by eye cup 3. A collimating lens 2 is provided immediately below the safety glass lens 7, located between the user's eye and the safety glass lens 7, or it can be combined with enlarging lens 8. The image generating device 4 is projected from above the safety glass lens 7 to provide an image to the user's eye. The image is provided to the eye in a narrow width in a light shielded chamber so that the image can be viewed simultaneously with the ambient environment.

The configuration of the image generating device is more clearly shown in FIG. 6b. A television screen 4 is set up above an optical device 6 which can be a beam splitter, mirror or screen. The screen 4 and optical device 6 are contained within a housing 5 which is sealed to light. The image travels from the screen 4 to the device 6 which reflects or partially reflects the image toward the eye cup end of the housing. The eye cup 3 stabilizes the interface between the housing 5 and the user's eye. Optionally, an enlarging lens 8 can be provided in the path between the television screen 4 and the optical device 6 to permit enlargement of the image before it is delivered to the user's eye.

Figure 7:
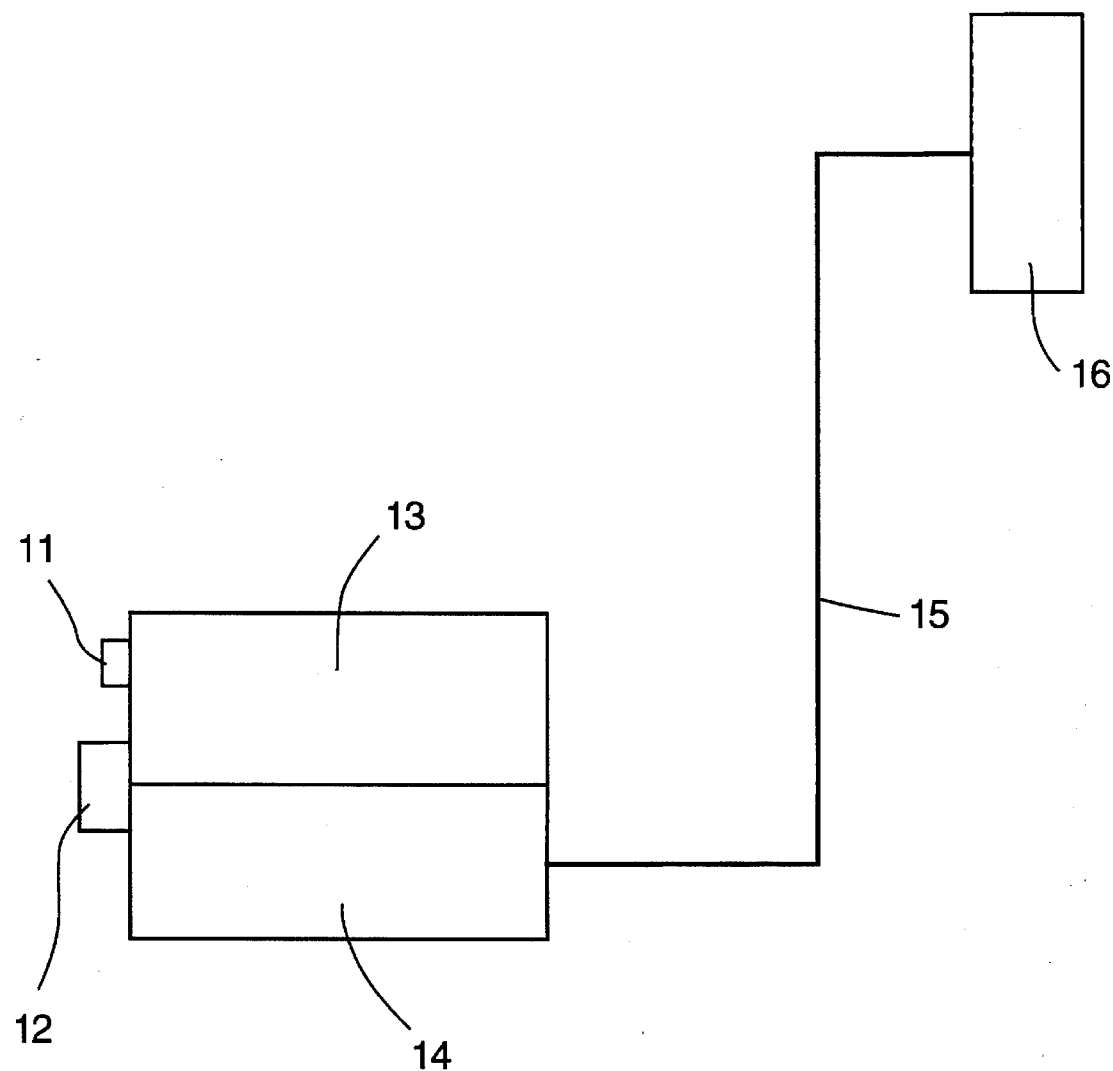
FIG. 7 is a block diagram of the components of the VIRTUAL VISION™ sport eyewear.

The collimating lens 2 is shown in FIG. 6c as having a convex surface so that the image can be widened or enlarged to generate a widened image. This configuration of collimating lens is used to provide a narrow obstruction to the field of view while providing an enlarged cue image. FIG. 6d shows the view of the device from the user's perspective, through the collimating lens 2 and the safety glass lens 7. The image generating television screen 4 is positioned above the user's field of view. The main components of the VIRTUAL VISION™ sport eyewear as described in Virtual Vision, Inc.'s brochure are shown in FIG. 7. The main components include video and stereo audio input jacks 11, a TV antenna 12, a TV receiver 13, a standard camcorder battery 14, a cord 15, and the VIRTUAL VISION™ headset 16. This system can be used to receive and to deliver virtual cues to the subject's eye. Other method of delivering video input to TV receiver are well known to those skilled in the art. This specific example is intended to illustrate the present invention and is not intended to limit the scope of the claims.

The common characteristic that gait enabling cues share is the ability to generate the perception to the subject that he is moving forward in the environment. For this reason the virtual cues must scroll toward the subject, much the same way as the dotted lines on a highway appear to scroll towards the driver of the car. The virtual cues serve as markers or reference points on the real world and convince the subject that he is moving forward. As an alternative to using geometric shapes as virtual markers on the real world, a virtual image of the real world itself could also be used to overcome dyskinesia, akinesia and sustain gait.

EXAMPLE 1

The following image is generated to the subject's non-dominant eye. The image is a picture of the real world as the subject sees it at a given point in time. The image is dynamically enlarged. The effect is identical to looking at the world through a telephoto lens while zooming back to the wide angle position on the lens. The subject will perceive herself as moving forward. The image of the real world would be updated or resampled at a frequency that would adjust for the subject's speed of ambulation.

Enabling hardware for this embodiment would consist of a large field of view image displaying device, e.g., VIRTUAL VISION™ sport eyewear. An attached small video camera with a programmable motorized telephoto-wide angle lens would be used to provide the kinetic virtual image of the real world as described above.

The test described below were performed using the VIRTUAL VISION™ sport eyewear which was specially modified for this application, not using the device shown in FIG. 6. This product is designed for entertainment and consists of a small color television in the brow piece of a device which looks like skiwear. The device provides the television image projected onto reality without obliterating the real world. The off the shelf version of this device was modified by dropping the television monitor out of the brow piece and into the frontal plane of the user's eye. A lens in front of the screen enlarges the perceived screen size. In order to obtain the minimum field of view required (adequate to see two cues with the necessary intercue distance, one must modify the standard equipment by removing the earpieces and nose support. The glasses must then be rotated 90° degrees and held with the lens as close to the non-dominant eye as possible. This places the longer horizontal axis of the screen in line with the direction of ambulation. The receiver is then detached from the battery pack to minimize weight and a lightweight camcorder is used as a video source for cueing images. The subject then positions his head to fine tune the position of the cues. He then times the scrolling cues so as to synchronize his gait with the cue.

EXAMPLE 2

MS is a 57 year old recently retired executive who has had Parkinson's Disease for fourteen (14) years. He is medicated using a combination of Sinemet CR and 25–100 totaling 2600 mg of dopamine each day. In addition he takes Permax. When we first met him he was extremely dyskinetic. His walk was grossly distorted and he got around his house using a battery-driven scooter. He was initially tested with playing cards placed on the floor. Within one step 90% of his dyskinesia was suppressed and his walk appeared very near to normal. Virtual cues were then applied using the VIRTUAL VISION™ sport eyewear after a short period of learning (2 or 3 steps), the same results were obtained. An hour later he was totally akinetic and responded dramatically to both the cards and virtual cues. He even was able to run using the cards.

EXAMPLE 3

NT is a 73 year old male with a history of Parkinson's Disease for 11 years and is medicated with an infusion pump. The identical tests were performed with the identical findings and results.

While the invention has been described above with reference to specific examples, these examples are intended to illustrate the present invention and are not intended to limit the scope of the claims below.

I claim:

1. A method for the treatment of gait problems associated with Parkinson's Disease in a subject which comprises the steps of:

a) providing an apparatus to be worn by the subject during treatment of gait problem associated with Parkingson's disease; which delivers optical images to the subject's view without disturbing the subject's visual perception of the subject's physical environment;

b) delivering an initiating cue to the subject through the optical image apparatus to initiate ambulation when needed; and, c) delivering sustaining cues to the subject through the optical image apparatus as needed to sustain ambulation once initiated.

2. The method of claim 1 wherein said optical image apparatus is selected from the group of devices consisting of video camera viewfinder in combination with cue images, a mechanical device which scrolls targets in the subject's field of vision, objects affixed to eyeglasses, cue cards affixed to the subject's footgear, and virtual reality headwear which provides electronically generated images to the subject's field of vision while allowing continued perception of the subject's physical environment.

3. The method of claim 1 wherein the initiating cue is static and appears as an object directly in front of the subject's toes as he stands ready to ambulate.

4. The method of claim 1 wherein the sustaining cues are kinetic and scroll toward the subject at a rate synchronized to the subject's rate of ambulation and with intercue distance appropriate to the subject's stride length.

5. An apparatus for use in the treatment of gait problems associated with Parkinson's Disease in a subject which comprises:
   a) virtual reality headwear including means for providing video-based imagery to the subject's field of vision while allowing continued visual perception of the subject's physical environment;
   b) means for delivering a video-based gait initiating cue to the subject during treatment through the virtual reality headwear to initiate ambulation; and
   c) means for delivering a video-based gait sustaining cues to the subject during treatment through the virtual reality headwear to sustain ambulation.

6. The apparatus of claim 5 wherein said cue delivering means employs graphic-based virtual cues as the video-based imagery for initiating and/or sustaining gait in the subject under treatment.

7. The apparatus of claim 5 wherein said cue delivering means employs actual real-world cues viewed through the lens of a video camera as the video-based imagery for initiating and/or sustaining gait in the subject under treatment.

8. The apparatus of claim 5 wherein said cue delivering means employs the subject's actual physical environment and a lens which dynamically enlarges the image of the physical environment as the video-based imagery for initiating and/or sustaining gait in the subject under treatment.

\* \* \* \* \*